US009763447B2

(12) United States Patent
Satchivi et al.

(10) Patent No.: US 9,763,447 B2
(45) Date of Patent: Sep. 19, 2017

(54) SAFENING 6-AMINO-2-(SUBSTITUTED PHENYL)-5-SUBSTITUTED-4-PYRIMIDINECARBOXYLATE HERBICIDE INJURY ON CEREAL CROPS

(71) Applicant: Dow AgroSciences LLC, Indianapolis, IN (US)

(72) Inventors: Norbert M. Satchivi, Carmel, IN (US); Paul Richard Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/208,008

(22) Filed: Jul. 12, 2016

(65) Prior Publication Data

US 2016/0316745 A1 Nov. 3, 2016

Related U.S. Application Data

(63) Continuation of application No. 12/913,879, filed on Oct. 28, 2010, now Pat. No. 9,408,387.

(60) Provisional application No. 61/256,021, filed on Oct. 29, 2009.

(51) Int. Cl.
*A01N 43/54* (2006.01)
*A01N 25/32* (2006.01)

(52) U.S. Cl.
CPC .................................... *A01N 43/54* (2013.01)

(58) Field of Classification Search
CPC ................................ A01N 25/32; A01N 43/54
See application file for complete search history.

(56) References Cited

U.S. PATENT DOCUMENTS

| | | | | |
|---|---|---|---|---|
| 4,639,266 A * | 1/1987 | Heubach | A01N 25/32 | 504/105 |
| 5,700,758 A * | 12/1997 | Rosch | A01N 25/32 | 504/106 |
| 6,884,757 B2 | 4/2005 | Ziemer et al. | | |
| 7,101,827 B2 | 9/2006 | Ziemer et al. | | |
| 7,300,907 B2 | 11/2007 | Epp et al. | | |
| 2007/0179059 A1 | 8/2007 | Epp et al. | | |
| 2009/0062121 A1 | 3/2009 | Satchivi et al. | | |
| 2009/0062125 A1 | 3/2009 | Epp et al. | | |
| 2009/0088322 A1 | 4/2009 | Epp et al. | | |

FOREIGN PATENT DOCUMENTS

| | | | |
|---|---|---|---|
| EP | 2191716 | A1 | 6/2010 |
| WO | 02085120 | | 10/2002 |
| WO | 2007082076 | A1 | 7/2007 |
| WO | 2007082098 | A2 | 7/2007 |
| WO | 2007120706 | A2 | 10/2007 |
| WO | 2009029735 | A1 | 3/2009 |
| WO | PCT/US10/054391 | | 10/2010 |

OTHER PUBLICATIONS

Office Action Issued in related EP Application No. 10776227.0 on Nov. 24, 2014.
Office Action Issued in related JP Application No. 2012-537021 on Dec. 16, 2014.
Office Action Issued in related JP Application No. 2012-537021 on Apr. 14, 2015.
Office Action Issued in related AU Application No. 2010319914 on Jan. 23, 2014.
Office Action Issued in related AU Application No. 2010319914 on Feb. 17, 2015.

* cited by examiner

*Primary Examiner* — John Pak
*Assistant Examiner* — Andriae M Holt
(74) *Attorney, Agent, or Firm* — Michael J. Terapane; Meunier Carlin & Curfman, LLC

(57) ABSTRACT

Herbicidal injury caused by 6-amino-2-(substituted phenyl)-5-substituted-4-pyrimidinecarboxylates in wheat and barley is reduced with the use of a safener selected from the group consisting of cloquintocet, fenchlorazole, mefenpyr and mixtures thereof.

18 Claims, No Drawings

SAFENING 6-AMINO-2-(SUBSTITUTED PHENYL)-5-SUBSTITUTED-4-PYRIMIDINECARBOXYLATE HERBICIDE INJURY ON CEREAL CROPS

FIELD OF THE INVENTION

This application is a continuation of U.S. application Ser. No. 12/913,879, filed Oct. 28, 2010, and claims the benefit of U.S. Provisional Application Ser. No. 61/256,021 filed on 29 Oct. 2009. This invention concerns the safening of the herbicidal injury cause by 6-amino-2-(substituted phenyl)-5-substituted-4-pyrimidine-carboxylates in cereal crops.

BACKGROUND OF THE INVENTION

When agrochemicals, such as plant protection agents and especially herbicides, are used, the cultivated plants may be damaged to a certain degree, depending on factors such as the dose of agrochemicals and their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree when an effective dose of herbicide is used. Various substances which are capable of specifically preventing the adverse effect of an herbicide on the cultivated plants, i.e. of protecting the cultivated plants without at the same time noticeably influencing the herbicidal action on weeds to be combated, have been proposed to solve this problem. However, it has been found that the antidotes proposed frequently have only a narrow field of use, i.e., a particular antidote is frequently suitable only for use with individual species of cultivated plants and/or for protecting the cultivated plants from individual herbicidal substances or classes of substances.

U.S. Patent Publications 2009/088322 and 2009/062125 and U.S. Patent 7,300,907 B2 describe certain 6-amino-2-(substituted phenyl)-5-substituted-4-pyrimidinecarboxylate compounds and their use as herbicides. While certain of these compounds have recently been found to be particularly effective herbicides for controlling undesirable vegetation in cereal crops, they have also been found to produce slight amounts of damage to both wheat and barley at concentrations required to adequately control the undesirable vegetation.

SUMMARY OF THE INVENTION

It has now been found that, surprisingly, the phytotoxic effect on wheat and barley of certain 6-amino-2-(substituted phenyl)-5-substituted-4-pyrimidinecarboxylate compounds, which have an auxinic mode of action, can be ameliorated by the use of certain safeners. The present invention concerns a method of protecting cereal crops from the harmful effects of a 6-amino-2-(substituted phenyl)-5-substituted-4-pyrimidinecarboxylate herbicide of the formula (I)

(I)

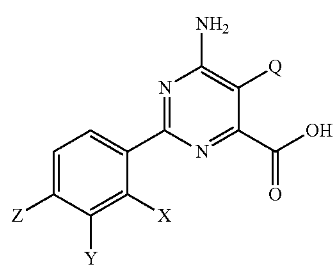

wherein

Q represents a $C_2$-$C_4$ alkenyl, $C_1$-$C_4$ alkoxy or halogen;

X represents H or halogen;

Y represents H, halogen, $C_1$-$C_4$ alkoxy, or —$NR_1R_2$;

Z represents halogen, $C_1$-$C_4$ alkyl or $C_1$-$C_4$ haloalkyl; and $R_1$ and $R_2$ independently represent H or $C_1$-$C_4$ alkyl;

and agriculturally acceptable salt, ester and amide derivatives of the carboxylic acid group which comprises contacting the cereal crops with, or applying to the area under cultivation, in addition to the 6-amino-2-(substituted phenyl)-5-substituted-4-pyrimidinecarboxylate herbicide, a safener selected from the group consisting of cloquintocet, fenchlorazole, mefenpyr and mixtures thereof.

Preferred compounds of formula (I) independently include those in which Q represents Cl, —CH=$CH_2$ or —$OCH_3$; X represents H or F; Y represents H, F, —$OCH_3$ or —$N(CH_3)_2$; and Z represents Cl, —$CH_3$, or —$CF_3$. The preferred safener is cloquintocet, particularly the mexyl ester.

The present invention also concerns a composition for protecting wheat and barley from the harmful effects of a 6-amino-2-(substituted phenyl)-5-substituted-4-pyrimidinecarboxylate herbicide of the formula (I)

(I)

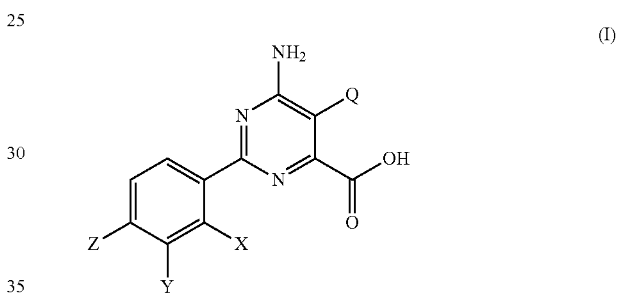

wherein

Q represents a $C_2$-$C_4$ alkenyl, $C_1$-$C_4$ alkoxy or halogen;

X represents H or halogen;

Y represents H, halogen, $C_1$-$C_4$ alkoxy, or —$NR_1R_2$;

Z represents halogen, $C_1$-$C_4$ alkyl or $C_1$-$C_4$ haloalkyl; and $R_1$ and $R_2$ independently represent H or $C_1$-$C_4$ alkyl;

and its agriculturally acceptable salt, ester and amide derivatives which comprises, in addition to the 6-amino-2-(substituted phenyl)-5-substituted-4-pyrimidinecarboxylate herbicide, a safener selected from the group consisting of cloquintocet, fenchlorazole, mefenpyr, and mixtures thereof.

It has now been found that, surprisingly, the phytotoxic effect on wheat and barley of certain 6-amino-2-(substituted phenyl)-5-substituted -4-pyrimidinecarboxylate herbicides, which have an auxinic mode of action, can be ameliorated by the use of cloquintocet at very low rates. For example, it has been surprisingly found that the use of cloquintocet in composition with a pyrimidinecarboxylate herbicide of the formula (I) exhibits a protecting effect against the phytotoxicity of the pyrimidinecarboxylate herbicide of formula (I) on spring and winter wheat (*Triticum aestivunz* L; TRZAS, TRZAW), durum wheat (*Trificum durum* L; TRZDU) and, spring and winter barley (*Hordeum vulgate* L; HORVS, HORVW) at herbicide-to-safener ratios between 16:1 and 1:1 without losing the herbicidal effects on weeds such as kochia (*Kochia scoparia* L; KCHSC), corn poppy (*Papaver rhoeas* L; PAPRH), bird's-eye speedwell (*Veronica persica* L; VERPE).

It has also been unexpectedly found that the mixture of phenyl pyrazole safeners such as fenchlorazole-ethyl and mefenpyr-diethyl with a pyrimidinecarboxylate herbicide of formula (I) shows a safening effect against the phytotoxicity of the pyrimidinecarboxylate herbicide of formula (I) on wheat (*Triticum aestivum* L; TRZAS) and barley (*Hordeum vulgare* L; HORVS) without reducing the herbicidal effects on weeds such as purple deadnettle (*Lamium purpureum* L; LAMPU), lamb's-quarters (*Chenopodium album* L; CHEAL).

DETAILED DESCRIPTION OF THE INVENTION

The pyrimidine carboxylic acids of formula (1) are a new class of compounds having herbicidal activity. A number of pyrimidine carboxylic acid compounds are described in U.S. Pat. No. 7,300,907 B2, U.S. Patent Application Publication 2009/088322 A1 and U.S. Patent Application Publication 2009/062125 A1, including 6-amino-5-chloro-2-(4-chloro-2-fluoro-3-methoxyphenyl)pyrimidine-4-carboxylic acid (Compound 1); 6-amino-2-(4-chloro-2-fluoro-3-methoxyphenyl)-5-vinylpyrimidine-4-carboxylic acid (Compound 2); 6-amino-2-(4-trifluoromethylphenyl)-5-methoxypyrimidine-4-carboxylic acid (Compound 3); 6-amino-2-(4-chloro-2-fluoro-3-methoxyphenyl)-5-methoxypyrimidine-4-carboxylic acid methyl ester (Compound 4); 6-amino-2-(4-chloro-2-fluoro-3-methoxyphenyl)-5-vinylpyrimidine-4-carboxylic acid methyl ester (Compound 5); 6-amino-2-p-tolyl-5-methoxypyrimidine-4-carboxylic acid (Compound 6); 6-amino-2-(4-chloro-3-dimethylamino-2-fluorophenyl)-5-vinylpyrimidine-4-carboxylic acid (Compound 7); 6-amino-2-(4-chloro-2-fluoro-3-methoxyphenyl)-5-methoxypyrimidine-4-carboxylic acid (Compound 8); 6-amino-2-(4-chloro-3-fluorophenyl)-5-methoxypyrimidine-4-carboxylic acid (Compound 9); and 6-amino-2-(4-chloro-2,3-difluorophenyl)-5-methoxypyrimidine-4-carboxylic acid (Compound 10). The pyrimidine carboxylic acids of formula (I) control annual grass weeds and broadleaf weeds in wheat and barley but are also phytotoxic to wheat and barley at commercially herbicidal doses.

Cloquintocet is the common name for [(5-chloro-8-quinolinyl)oxy]acetic acid; it is frequently used as the 1-methylhexyl ester (mexyl). Its safening activity is described in *The Pesticide Manual*, Fourteenth Edition, 2006. Cloquintocet is used as a safener in cereals.

Fenchlorazole is the common name for 1-(2,4-dichlorophenyl)-5-(trichloromethyl)-1H-1,2,4-triazole-3-carboxylic acid. Its safening activity is described in *The Pesticide Manual*, Fourteenth Edition, 2006. Fenchlorazole is used as a safener in wheat, rye and triticale.

Mefenpyr is the common name for 1-(2,4-dichlorophenyl)-4,5-dihydro-5-methyl-1H-pyrazole-3,5-dicarboxylic acid. Its safening activity is described in *The Pesticide Manual,* Fourteenth Edition, 2006. Mefenpyr is used as a safener in wheat, rye, triticale and barley.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

Cultivated plants which are to be protected from the adverse effect of undesirable plant growth may be damaged to a certain degree when an effective dose of herbicide is used. Safening means preventing the adverse effect of an herbicide on the cultivated plants, i.e., protecting the cultivated plants without, at the same time, noticeably influencing the herbicidal action on weeds to be combated.

In the composition of this invention, the weight ratio of the safener to the pyrimidine carboxylic acid of formula (I) at which the herbicidal effect on the cultivated plant is safened lies within the range of between about 1:16 and about 4:1. Preferably, the weight ratio of cloquintocet to the pyrimidine carboxylic acid of formula (I) at which the herbicidal effect on the cultivated plant is safened lies within the range of between about 1:4 and about 2:1.

The rate at which the safened composition is applied will depend upon the particular type of weed to be controlled, the degree of control required, and the timing and method of application. In general, the composition of the invention can be applied at an application rate of between about 1 gram per hectare (g/ha) and about 280 g/ha based on the total amount of pyrimidine carboxylic acid of formula (I) and safener in the composition.

The pyrimidine carboxylic acid of formula (I) and the safener of the present invention can be applied either separately or together as part of a multipart herbicidal system.

The herbicide-safener mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the safened composition of the present invention include 2,4-D, amidosulfuron, beflubutamid, benazolin, bentazone, bifenox, bromoxynil, butachlor, butafenacil, carfentrazone-ethyl, chlormequat, chlortoluron, cinidon-ethyl, clodinafop-propargyl, clopyralid, cyanazine, cyclosulfamuron, dicamba, diclofop-methyl, diflufenican, diflufenzopyr, dimefuron, diuron, ethoxysulfuron, fenoxaprop, fenoxaprop-ethyl, fenoxaprop-ethyl+ isoxidifen-ethyl, fenoxaprop-p-ethyl, florasulam, flucarbazone, flucetosulfuron (LGC-421530, flufenacet, flumetsulam, flupyrsulfuron, flurtamone, imazamethabenz, imazamox, imazapic, imazapyr, imazaquin, imazethapyr, imazosulfuron, indanofan, iodosulfuron, iodosulfuron-ethyl-sodium, ioxynil, isoproturon, isoxaben, lactofen, linuron, MCPA, mecoprop-P, mesosulfuron, mesosulfuron-ethyl sodium, metosulam, metribuzin, metsulfuron, metsulfuron-methyl, orthosulfamuron, oxyfluorfen, pendimethalin, penoxsulam, picolinafen, pinoxaden, primisulfuron, profluazol, propoxycarbazone, prosulfocarb, prosulfuron, pyraflufen ethyl, pyribenzoxim (LGC-40863), pyroxasulfone, pyroxsulam, quinmerac, sulfosulfuron, thifensulfuron, thifensulfuron-methyl, topramezone, tralkoxydim, triasulfuron, tribenuron, and tribenuron-methyl.

The safened composition of the present invention can, further, be used in conjunction with glyphosate, glufosinate, dicamba, imidazolinones, sulfonylureas or 2,4-D on glyphosate-tolerant, glufosinate-tolerant, dicamba-tolerant, imidazolinone-tolerant, sulfonylurea-tolerant or 2,4-D-tolerant crops. It is generally preferred to use the herbicide-safener mixture of the present invention in combination with herbicides that are selective for the crop being treated and which complement the spectrum of weeds controlled by these compounds at the application rate employed. It is further generally preferred to apply the safened composition of the present invention and other complementary herbicides at the same time, either as a combination formulation or as a tank mix.

In practice, it is preferable to use the safened composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+ emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+ urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylcnc glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., N.Y., 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicide-safener mixture of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to paddy or irrigation water, and by other conventional means known to those skilled in the art.

The following examples illustrate the present invention.

Evaluation of Postemergence Herbicidal Safening in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 18° C. during the day and 17 ° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the acids or esters of compounds 1-10 and cloquintocet-mexyl (CQC-M), fenchlorazole-ethyl, mefenpyr-diethyl alone and in combination. Weighed amounts of acid or methyl esters of the compounds of formula (I) were dissolved in a volume of 97:3 v/v acetone/dimethylsulfoxide (DMSO) to obtain concentrated solutions. If the test compound did not dissolve readily, the mixture was warmed and/or sonicated. The concentrated solutions of the test compound were diluted with the addition of an aqueous mixture containing acetone, water, isopropyl alcohol, DMSO, Agri-Dex crop oil concentrate, and Triton® X-77 surfactant in a 64.7:26.0:6.7:2.0:0.7:0.01 v/v ratio. Test compounds were diluted to the appropriate application rate with a dilution solution which was prepared by mixing the appropriate volume of 97:3 v/v acetone/DMSO and the appropriate volume of an aqueous mixture containing acetone, water, isopropyl alcohol, DMSO, Agri-Dex crop oil concentrate, and Triton® X-77 surfactant in a 64.7:26.0:6.7:2.0:0.7:0.01 v/v ratio. Compound requirements are based upon a 12 nit application volume at a rate of 187 liters per hectare (L/ha). The concentrated solutions of the safener were prepared following the same procedure.

18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected}=A+B-(A\times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 1 through Table 24.

TABLE 1

Safening Activity of Herbicidal Compositions on Wheat and Barley

| Application rate (g/ha) | | | TRZAS | | TRZAW | | TRZDU | | HORVS | | HORVW | | AMARE | | GALAP | | LAMPU | |
|---|---|---|---|---|---|---|---|---|---|---|---|---|---|---|---|---|---|---|
| Compound 1 | CQC-M | Ratio | Ob | Ex | Ob | Ex | Ob | Ex | Ob | Ex | Ob | Ex | Ob | Ex | Ob | Ex | Ob | Ex |
| 70 | 0 | | 25 | — | 35 | — | 15 | — | 15 | — | 15 | — | 100 | — | 95 | — | 95 | — |
| 140 | 0 | | 45 | — | 40 | — | 35 | — | 30 | — | 40 | — | 100 | — | 95 | — | 99 | — |
| 0 | 35 | | 0 | — | 0 | — | 0 | — | 0 | — | 0 | — | 0 | — | 0 | — | 0 | — |
| 0 | 70 | | 0 | — | 0 | — | 15 | — | 0 | — | 0 | — | 0 | — | 0 | — | 0 | — |
| 0 | 140 | | 0 | — | 0 | — | 20 | — | 0 | — | 0 | — | 0 | — | 0 | — | 0 | — |
| 70 | 35 | 2:1 | 0 | 25 | 0 | 35 | 0 | 15 | 0 | 15 | 0 | 15 | 100 | 100 | 95 | 95 | 99 | 95 |
| 70 | 70 | 1:1 | 0 | 25 | 0 | 35 | 0 | 28 | 0 | 15 | 0 | 15 | 100 | 100 | 95 | 95 | 99 | 95 |
| 140 | 70 | 2:1 | 5 | 45 | 0 | 40 | 40 | 45 | 0 | 30 | 0 | 40 | 100 | 100 | 95 | 95 | 95 | 99 |
| 140 | 140 | 1:1 | 0 | 45 | 0 | 40 | 45 | 48 | 0 | 30 | 0 | 40 | 100 | 100 | 95 | 95 | 95 | 99 |

TABLE 2

Safening Activity of Herbicidal Compositions on Wheat and Barley

| Application Rate (g/ha) | | | TRZAS | | HORVS | | TRZAW | | HORVW | | TRZDU | | KCHSC | | PAPRH | | VERPE | |
|---|---|---|---|---|---|---|---|---|---|---|---|---|---|---|---|---|---|---|
| Compound 2 | CQC-M | Ratio | Ob | Ex | Ob | Ex | Ob | Ex | Ob | Ex | Ob | Ex | Ob | Ex | Ob | Ex | Ob | Ex |
| 8.75 | 0 | | 41 | — | 24 | — | 43 | — | 18 | — | 30 | — | 40 | — | 80 | — | 70 | — |
| 0 | 0.547 | | 0 | — | 0 | — | 0 | — | 0 | — | 0 | — | — | — | — | — | — | — |
| 0 | 8.75 | | 0 | — | 0 | — | — | — | — | — | — | — | 0 | — | 0 | — | 0 | — |
| 8.75 | 0.547 | 16:1 | 0 | 41 | 3 | 24 | 0 | 43 | 3 | 18 | 0 | 30 | — | — | — | — | — | — |
| 8.75 | 8.75 | 1:1 | 0 | 41 | 0 | 24 | — | — | — | — | — | — | 60 | 40 | 70 | 80 | 65 | 70 |

Weighed amounts of safener were dissolved in a volume of 97:3 v/v acetone/DMSO to obtain concentrated safener solutions.

Spray solutions of the herbicide safener and test compound mixtures were prepared by adding the concentrated solutions to the appropriate amount of dilution solution to form 12 mL spray solution with active ingredients in combinations.

Formulated compounds were applied to the plant material with an overhead Mandel track sprayer equipped with 8002E nozzles calibrated to deliver 187 L/ha over an application area of 0.503 square meters ($m^2$) at a spray height of

TABLE 3

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 2 | Fenchlorazole-ethyl | Ratio | Ob | Ex | Ob | Ex | Ob | Ex |
| 35 | 0 | | 80 | — | 68 | — | 77 | — |
| 0 | 140 | | 0 | — | 0 | — | 0 | — |
| 35 | 140 | 1:4 | 18 | 80 | 12 | 68 | 90 | 77 |

TABLE 4

| Safening Activity of Herbicidal Compositions on Wheat and Barley | | | | | | | | |
|---|---|---|---|---|---|---|---|---|
| Application Rate (g ae/ha) | | | TRZAS | | HORVS | | LAMPU | |
| Compound 2 | Mefenpyr-diethyl | Ratio | Ob | Ex | Ob | Ex | Ob | Ex |
| 35 | 0 | | 80 | — | 68 | — | 77 | — |
| 0 | 140 | | 0 | — | 0 | — | 0 | — |
| 35 | 140 | 1:4 | 13 | 80 | 10 | 68 | 90 | 77 |

TABLE 5

| Safening Activity of Herbicidal Compositions on Wheat and Barley | | | | | | | | | | | | |
|---|---|---|---|---|---|---|---|---|---|---|---|---|
| Application Rate (g/ha) | | | TRZAS | | HORVS | | TRZAW | | HORVW | | TRZDU | |
| Compound 3 | CQC-M | Ratio | Ob | Ex | Ob | Ex | Ob | Ex | Ob | Ex | Ob | Ex |
| 8.75 | 0 | — | 15 | — | 13 | — | 17 | — | 8 | — | 7 | — |
| 0 | 2.1875 | — | 0 | — | 0 | — | 0 | — | 0 | — | 0 | — |
| 0 | 8.75 | — | 0 | — | 0 | — | 0 | — | 0 | — | 0 | — |
| 0 | 35 | — | 0 | — | 0 | — | 0 | — | 0 | — | 0 | — |
| 8.75 | 2.1875 | 4:1 | 0 | 15 | 0 | 13 | 2 | 17 | 0 | 8 | 0 | 7 |
| 8.75 | 8.75 | 1:1 | 0 | 15 | 0 | 13 | 0 | 17 | 0 | 8 | 0 | 7 |
| 8.75 | 35 | 1:4 | 2 | 15 | 2 | 13 | 3 | 17 | 0 | 8 | 0 | 7 |

TABLE 6

| Safening Activity of Herbicidal Compositions on Wheat and Barley | | | | | | | | |
|---|---|---|---|---|---|---|---|---|
| Application Rate (g ae/ha) | | | TRZAS | | HORVS | | CHEAL | |
| Compound 3 | Fenchlorazole-ethyl | Ratio | Ob | Ex | Ob | Ex | Ob | Ex |
| 35 | 0 | | 75 | — | 50 | — | 10 | — |
| 0 | 140 | | 0 | — | 0 | — | 0 | — |
| 35 | 140 | 1:4 | 40 | 75 | 23 | 50 | 10 | 10 |

TABLE 7

| Safening Activity of Herbicidal Compositions on Wheat and Barley | | | | | | | | |
|---|---|---|---|---|---|---|---|---|
| Application Rate (g ae/ha) | | | TRZAS | | HORVS | | CHEAL | |
| Compound 3 | Mefenpyr-diethyl | Ratio | Ob | Ex | Ob | Ex | Ob | Ex |
| 35 | 0 | | 75 | — | 50 | — | 10 | — |
| 0 | 140 | | 0 | — | 0 | — | 0 | — |
| 35 | 140 | 1:4 | 38 | 75 | 35 | 50 | 10 | 10 |

TABLE 8

| Safening Activity of Herbicidal Compositions on Wheat and Barley | | | | | | | | | | | | |
|---|---|---|---|---|---|---|---|---|---|---|---|---|
| Application Rate (g/ha) | | | TRZAS | | HORVS | | TRZAW | | HORVW | | TRZDU | |
| Compound 4 | CQC-M | Ratio | Ob | Ex | Ob | Ex | Ob | Ex | Ob | Ex | Ob | Ex |
| 8.75 | 0 | | 33 | — | 25 | — | 22 | — | 7 | — | 18 | — |
| 0 | 2.1875 | | 0 | — | 0 | — | 0 | — | 0 | — | 0 | — |
| 0 | 8.75 | | 0 | — | 0 | — | 0 | — | 0 | — | 0 | — |
| 0 | 35 | | 0 | — | 0 | — | 0 | — | 0 | — | 0 | — |
| 8.75 | 2.1875 | 4:1 | 2 | 33 | 3 | 25 | 0 | 22 | 0 | 7 | 5 | 18 |
| 8.75 | 8.75 | 1:1 | 0 | 33 | 0 | 25 | 2 | 22 | 2 | 7 | 0 | 18 |
| 8.75 | 35 | 1:4 | 0 | 33 | 0 | 25 | 5 | 22 | 3 | 7 | 3 | 18 |

TABLE 9

| Safening Activity of Herbicidal Compositions on Wheat and Barley | | | | | | | | |
|---|---|---|---|---|---|---|---|---|
| Application Rate (g ae/ha) | | | TRZAS | | HORVS | | LAMPU | |
| Compound 4 | Fenchlorazole-ethyl | Ratio | Ob | Ex | Ob | Ex | Ob | Ex |
| 35 | 0 | | 80 | — | 75 | — | 100 | — |
| 0 | 140 | | 0 | — | 0 | — | 0 | — |
| 35 | 140 | 1:4 | 20 | 80 | 10 | 75 | 100 | 100 |

TABLE 10

| Safening Activity of Herbicidal Compositions on Wheat and Barley | | | | | | | | |
|---|---|---|---|---|---|---|---|---|
| Application Rate (g ae/ha) | | | TRZAS | | HORVS | | LAMPU | |
| Compound 4 | Mefenpyr-diethyl | Ratio | Ob | Ex | Ob | Ex | Ob | Ex |
| 35 | 0 | | 80 | — | 75 | — | 100 | — |
| 0 | 140 | | 0 | — | 0 | — | 0 | — |
| 35 | 140 | 1:4 | 20 | 80 | 15 | 75 | 100 | 100 |

TABLE 11

| Safening Activity of Herbicidal Compositions on Wheat and Barley | | | | | | | | | | | | |
|---|---|---|---|---|---|---|---|---|---|---|---|---|
| Application Rate (g/ha) | | | TRZAS | | HORVS | | CIRAR | | LAMPU | | PAPRH | |
| Compound 5 | CQC-M | Ratio | Ob | Ex | Ob | Ex | Ob | Ex | Ob | Ex | Ob | Ex |
| 70 | 0 | | 18 | — | 8 | — | 84 | — | 95 | — | 89 | — |
| 140 | 0 | | 40 | — | 0 | — | 85 | — | 95 | — | 90 | — |

TABLE 11-continued

Safening Activity of Herbicidal Compositions on Wheat and Barley

| Application Rate (g/ha) | | | TRZAS | | HORVS | | CIRAR | | LAMPU | | PAPRH | |
|---|---|---|---|---|---|---|---|---|---|---|---|---|
| Compound 5 | CQC-M | Ratio | Ob | Ex | Ob | Ex | Ob | Ex | Ob | Ex | Ob | Ex |
| 0 | 70 | | 0 | — | 0 | — | 0 | — | 0 | — | 0 | — |
| 0 | 140 | | 0 | — | 0 | — | 0 | — | 0 | — | 0 | — |
| 70 | 70 | 1:1 | 3 | 18 | 5 | 8 | 83 | 84 | 95 | 95 | 93 | 89 |
| 140 | 140 | 1:1 | 10 | 40 | 0 | 0 | 93 | 85 | 93 | 95 | 97 | 90 |

TABLE 12

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 5 | Fenchlorazole-ethyl | Ratio | Ob | Ex | Ob | Ex | Ob | Ex |
| 35 | 0 | | 25 | — | 10 | — | 75 | — |
| 0 | 140 | | 0 | — | 0 | — | 0 | — |
| 35 | 140 | 1:4 | 5 | 25 | 3 | 10 | 75 | 75 |

TABLE 13

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 5 | Mefenpyr-diethyl | Ratio | Ob | Ex | Ob | Ex | Ob | Ex |
| 35 | 0 | | 25 | — | 10 | — | 75 | — |
| 0 | 140 | | 0 | — | 0 | — | 0 | — |
| 35 | 140 | 1:4 | 5 | 25 | 5 | 10 | 75 | 75 |

TABLE 14

Safening Activity of Herbicidal Compositions on Wheat and Barley

| Application Rate (g/ha) | | | TRZAS | | HORVS | | KCHSC | | LAMPU | | PAPRH | |
|---|---|---|---|---|---|---|---|---|---|---|---|---|
| Compound 6 | CQC-M | Ratio | Ob | Ex | Ob | Ex | Ob | Ex | Ob | Ex | Ob | Ex |
| 70 | 0 | | 20 | — | 20 | — | 60 | — | 75 | — | 97 | — |
| 140 | 0 | | 55 | — | 40 | — | 70 | — | 80 | — | 100 | — |
| 0 | 70 | | 0 | — | 0 | — | 0 | — | 0 | — | 0 | — |
| 0 | 140 | | 0 | — | 0 | — | 0 | — | 0 | — | 0 | — |
| 70 | 70 | 1:1 | 10 | 20 | 10 | 20 | 65 | 60 | 70 | 75 | 97 | 97 |
| 140 | 140 | 1:1 | 5 | 55 | 10 | 40 | 70 | 70 | 85 | 80 | 95 | 100 |

TABLE 15

Safening Activity of Herbicidal Compositions on Wheat and Barley

| Application Rate (g ae/ha) | | | TRZAS | | HORVS | | CHEAL | |
|---|---|---|---|---|---|---|---|---|
| Compound 6 | Fenchlorazole-ethyl | Ratio | Ob | Ex | Ob | Ex | Ob | Ex |
| 35 | 0 | | 35 | — | 25 | — | 83 | — |
| 0 | 140 | | 0 | — | 0 | — | 0 | — |
| 35 | 140 | 1:4 | 3 | 35 | 3 | 25 | 83 | 83 |

TABLE 16

Safening Activity of Herbicidal Compositions on Wheat and Barley

| Application Rate (g ae/ha) | | | TRZAS | | HORVS | | CHEAL | |
|---|---|---|---|---|---|---|---|---|
| Compound 6 | Mefenpyr-diethyl | Ratio | Ob | Ex | Ob | Ex | Ob | Ex |
| 35 | 0 | | 35 | — | 25 | — | 83 | — |
| 0 | 140 | | 0 | — | 0 | — | 0 | — |
| 35 | 140 | 1:4 | 15 | 35 | 0 | 25 | 83 | 83 |

TABLE 17

Safening Activity of Herbicidal Compositions on Wheat and Barley

| Application Rate (g/ha) | | | TRZAS | | HORVS | | CIRAR | | KCHSC | | SASKR | |
|---|---|---|---|---|---|---|---|---|---|---|---|---|
| Compound 7 | CQC-M | Ratio | Ob | Ex | Ob | Ex | Ob | Ex | Ob | Ex | Ob | Ex |
| 70 | 0 | | 60 | — | 30 | — | 80 | — | 65 | — | 75 | — |
| 140 | 0 | | 70 | — | 45 | — | 85 | — | 75 | — | 80 | — |
| 0 | 70 | | 0 | — | 0 | — | 0 | — | 0 | — | 0 | — |
| 0 | 140 | | 0 | — | 0 | — | 0 | — | 0 | — | 0 | — |
| 70 | 70 | 1:1 | 0 | 60 | 0 | 30 | 80 | 80 | 60 | 65 | 80 | 75 |
| 140 | 140 | 1:1 | 0 | 70 | 0 | 45 | 87 | 85 | 95 | 75 | 80 | 80 |

TABLE 18

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 7 | Fenchlorazole-ethyl | Ratio | Ob | Ex | Ob | Ex | Ob | Ex |
| 35 | 0 | | 75 | — | 70 | — | 52 | — |
| 0 | 140 | | 0 | — | 0 | — | 0 | — |
| 35 | 140 | 1:4 | 20 | 75 | 12 | 70 | 50 | 52 |

TABLE 19

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 7 | Mefenpyr-diethyl | Ratio | Ob | Ex | Ob | Ex | Ob | Ex |
| 35 | 0 | | 75 | — | 70 | — | 52 | — |
| 0 | 140 | | 0 | — | 0 | — | 0 | — |
| 35 | 140 | 1:4 | 22 | 75 | 7 | 70 | 50 | 52 |

TABLE 20

Safening Activity of Herbicidal Compositions on Wheat and Barley

| Application Rate (g/ha) | | | TRZAS | | HORVS | | KCHSC | | LAMPU | | PAPRH | |
|---|---|---|---|---|---|---|---|---|---|---|---|---|
| Compound 8 | CQC-M | Ratio | Ob | Ex | Ob | Ex | Ob | Ex | Ob | Ex | Ob | Ex |
| 70 | 0 | | 90 | — | 50 | — | 90 | — | 100 | — | 100 | — |
| 140 | 0 | | 95 | — | 85 | — | 100 | — | 100 | — | 100 | — |
| 0 | 70 | | 0 | — | 0 | — | 0 | — | 0 | — | 0 | — |
| 0 | 140 | | 0 | — | 0 | — | 0 | — | 0 | — | 0 | — |
| 70 | 70 | 1:1 | 30 | 90 | 0 | 50 | 95 | 90 | 100 | 100 | 100 | 100 |
| 140 | 140 | 1:1 | 40 | 95 | 10 | 85 | 93 | 100 | 100 | 100 | 100 | 100 |

TABLE 21

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 8 | Fenchlorazole-ethyl | Ratio | Ob | Ex | Ob | Ex | Ob | Ex |
| 35 | 0 | | 83 | — | 75 | — | 100 | — |
| 0 | 140 | | 0 | — | 0 | — | 0 | — |
| 35 | 140 | 1:4 | 18 | 83 | 10 | 75 | 100 | 100 |

TABLE 22

Safening Activity of Herbicidal Compositions on Wheat and Barley

| Application Rate (g ae/ha) | | | TRZAS | | HORVS | | LAMPU | |
|---|---|---|---|---|---|---|---|---|
| Compound 8 | Mefenpyr-diethyl | Ratio | Ob | Ex | Ob | Ex | Ob | Ex |
| 35 | 0 | | 83 | — | 75 | — | 100 | — |
| 0 | 140 | | 0 | — | 0 | — | 0 | — |
| 35 | 140 | 1:4 | 20 | 83 | 10 | 75 | 100 | 100 |

TABLE 23

Safening Activity of Herbicidal Compositions on Wheat and Barley

| Application Rate (g/ha) | | | TRZAS | | HORVS | | KCHSC | | LAMPU | | MATCH | |
|---|---|---|---|---|---|---|---|---|---|---|---|---|
| Compound 9 | CQC-M | Ratio | Ob | Ex | Ob | Ex | Ob | Ex | Ob | Ex | Ob | Ex |
| 70 | 0 | | 60 | — | 50 | — | 100 | — | 95 | — | 93 | — |
| 140 | 0 | | 70 | — | 70 | — | 100 | — | 100 | — | 97 | — |
| 0 | 70 | | 0 | — | 0 | — | 0 | — | 0 | — | 0 | — |
| 0 | 140 | | 0 | — | 0 | — | 0 | — | 0 | — | 0 | — |
| 70 | 70 | 1:1 | 20 | 60 | 10 | 50 | 95 | 100 | 95 | 95 | 93 | 93 |
| 140 | 140 | 1:1 | 30 | 70 | 10 | 70 | 95 | 100 | 100 | 100 | 93 | 97 |

TABLE 24

Safening Activity of Herbicidal Compositions on Wheat and Barley

| Application Rate (g ae/ha) | | | TRZAS | | HORVS | | CIRAR | | KCHSC | | LAMPU | | MATCH | |
|---|---|---|---|---|---|---|---|---|---|---|---|---|---|---|
| Compound 10 | CQC-M | Ratio | Ob | Ex | Ob | Ex | Ob | Ex | Ob | Ex | Ob | Ex | Ob | Ex |
| 8.75 | 0 | | 45 | — | 25 | — | 80 | — | 98 | — | 95 | — | 70 | — |
| 17.5 | 0 | | 55 | — | 30 | — | 85 | — | 98 | — | 95 | — | 90 | — |
| 35 | 0 | | 65 | — | 60 | — | 90 | — | 100 | — | 100 | — | 93 | — |
| 70 | 0 | | 70 | — | 75 | — | 90 | — | 100 | — | 100 | — | 95 | — |
| 140 | 0 | | 75 | — | 85 | — | 100 | — | 100 | — | 100 | — | 100 | — |
| 0 | 8.75 | | 0 | — | 0 | — | 0 | — | 0 | — | 0 | — | 0 | — |
| 0 | 17.5 | | 0 | — | 0 | — | 0 | — | 0 | — | 0 | — | 0 | — |
| 0 | 35 | | 0 | — | 0 | — | 0 | — | 0 | — | 0 | — | 0 | — |
| 0 | 70 | | 0 | — | 0 | — | 0 | — | 0 | — | 0 | — | 0 | — |
| 0 | 140 | | 0 | — | 0 | — | 0 | — | 0 | — | 0 | — | 0 | — |
| 8.75 | 8.75 | 1:1 | 5 | 45 | 0 | 25 | 83 | 80 | 95 | 98 | 95 | 95 | 87 | 70 |
| 17.5 | 17.5 | 1:1 | 10 | 55 | 0 | 30 | 87 | 85 | 100 | 98 | 95 | 95 | 87 | 90 |
| 35 | 35 | 1:1 | 15 | 65 | 0 | 60 | 90 | 90 | 100 | 100 | 100 | 100 | 90 | 93 |
| 70 | 70 | 1:1 | 20 | 70 | 20 | 75 | 90 | 90 | 100 | 100 | 100 | 100 | 98 | 95 |
| 140 | 140 | 1:1 | 30 | 75 | 30 | 85 | 97 | 100 | 100 | 100 | 100 | 100 | 98 | 100 |

| Application Rate (g ae/ha) | | | PAPRH | | SASKR | | SINAR | | VERPE | | VIOTR | |
|---|---|---|---|---|---|---|---|---|---|---|---|---|
| Compound 10 | CQC-M | Ratio | Ob | Ex | Ob | Ex | Ob | Ex | Ob | Ex | Ob | Ex |
| 8.75 | 0 | | 100 | — | 85 | — | 100 | — | 93 | — | 70 | — |
| 17.5 | 0 | | 100 | — | 87 | — | 100 | — | 97 | — | 75 | — |
| 35 | 0 | | 100 | — | 90 | — | 100 | — | 100 | — | 85 | — |

TABLE 24-continued

| Safening Activity of Herbicidal Compositions on Wheat and Barley | | | | | | | | | | | | |
|---|---|---|---|---|---|---|---|---|---|---|---|---|
| 70 | 0 | | 100 | — | 93 | — | 100 | — | 100 | — | 93 | — |
| 140 | 0 | | 100 | — | 95 | — | 100 | — | 100 | — | 97 | — |
| 0 | 8.75 | | 0 | — | 0 | — | 0 | — | 0 | — | 0 | — |
| 0 | 17.5 | | 0 | — | 0 | — | 0 | — | 0 | — | 0 | — |
| 0 | 35 | | 0 | — | 0 | — | 0 | — | 0 | — | 0 | — |
| 0 | 70 | | 0 | — | 0 | — | 0 | — | 0 | — | 0 | — |
| 0 | 140 | | 0 | — | 0 | — | 0 | — | 0 | — | 0 | — |
| 8.75 | 8.75 | 1:1 | 100 | 100 | 85 | 85 | 100 | 100 | 93 | 93 | 85 | 70 |
| 17.5 | 17.5 | 1:1 | 100 | 100 | 87 | 87 | 100 | 100 | 100 | 97 | 83 | 75 |
| 35 | 35 | 1:1 | 100 | 100 | 90 | 90 | 100 | 100 | 100 | 100 | 87 | 85 |
| 70 | 70 | 1:1 | 100 | 100 | 93 | 93 | 100 | 100 | 100 | 100 | 90 | 93 |
| 140 | 140 | 1:1 | 100 | 100 | 97 | 95 | 100 | 100 | 100 | 100 | 93 | 97 |

TRZAS = *Triticum aestivum*, spring wheat
HORVS = *Hordeum vulgare*, spring barley
MATCH = *Matricaria chamomile*, scented mayweed
PAPRH = *Papaver rhoeas*, poppy
TRZAW = *Triticum aestivum*, winter wheat
GALAP = *Galium aparine*, cleavers
HORVW = *Hordeum vulgare*, winter barley
SASKR = *Salsola iberica*, Russian thistle
TRZDU = *Triticum durum*, durum wheat
CHEAL = *Chenopodium album*, lamb's-quarters
AMARE = *Amaranthus retroflexus*, redroot pigweed
SINAR = *Sinapis arvensis* L., wild mustard
CIRAR = *Cirsium arvense*, Canada thistle
VERPE = *Veronica persica*, bird's-eye speedwell
KCHSC = *Kochia scoparia*, kochia
VIOTR = *Viola tricolor*, wild pansy
LAMPU = *Lamium purpureum*, purple deadnettle
CQC-M = Cloquintocet-mexyl
Ob = Observed values (% control
Ex = Expected values (% control)

What is claimed is:

1. A composition for protecting wheat and barley from the harmful effects of a 6-amino-2-(substituted phenyl)-5-substituted-4-pyrimidinecarboxylate herbicide of the formula (I)

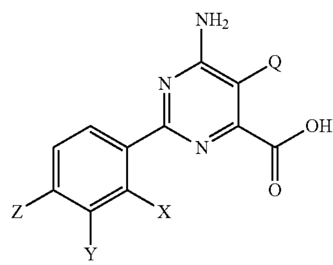

wherein:

Q represents a $C_2$-$C_4$ alkenyl or $C_1$-$C_4$ alkoxy;

X represents H or halogen;

Y represents H, halogen, $C_1$-$C_4$ alkoxy, or —$NR_1R_2$;

Z represents halogen, $C_1$-$C_4$ alkyl or $C_1$-$C_4$ haloalkyl; and $R_1$ and $R_2$ independently represent H or $C_1$-$C_4$ alkyl;

and its agriculturally acceptable salt, ester and amide derivatives, which comprises, in addition to the 6-amino-2-(substituted phenyl)-5-substituted-4-pyrimidinecarboxylate herbicide, a safener selected from the group consisting of fenchlorazole, fenchlorazole-ethty, mefenpyr, mefenpyr-diethyl, and mixtures thereof, wherein the weight ratio of the safener to 6-amino-2-(substituted phenyl)-5-substituted-4-pyrimidinecarboxylate herbicide is between 1:16 and 4:1.

2. The composition of claim 1 in which the weight ratio of the safener to 6-amino-2-(substituted phenyl)-5-substituted-4-pyrimidinecarboxylate herbicide is in the range of 1:4 to 2:1.

3. The composition of claim 1 in which the 6-amino-2-(substituted phenyl)-5-substituted-4-pyrimidinecarboxylate herbicide is selected from the group consisting of 6-amino-2-(4-chloro-2-fluoro-3-methoxyphenyl)-5-vinyl pyrimidine-4-carboxylic acid; 6-amino-2-(4-trifluoromethylphenyl)-5-methoxypyrimidine-4-carboxylic acid; 6-amino-2-(4-chloro-2-fluoro-3-methoxyphenyl)-5-methoxypyrimidine-4-carboxylic acid; 6-amino-2-p-tolyl-5-methoxypyrimidine-4-carboxylic acid; 6-amino-2-(4-chloro-3-dimethylamino-2-fluorophenyl)-5-vinylpyrimidine-4-carboxylic acid; 6-amino-2-(4-chloro-3-fluorophenyl)-5-methoxypyrimidine-4-carboxylic acid; 6-amino-2-(4-chloro-2,3-difluorophenyl)-5-methoxypyrimidine-4-carboxylic acid; and agriculturally acceptable salts, esters, or amides thereof.

4. The composition of claim 1, wherein Q represents a $C_2$-$C_4$ alkenyl.

5. The composition of claim 4 in which the 6-amino-2-(substituted phenyl)-5-substituted-4-pyrimidinecarboxylate herbicide is 6-amino-2-(4-chloro-2-fluoro-3-methoxyphenyl)-5-vinylpyrimidine-4-carboxylic acid methyl ester.

6. The composition of claim 1, wherein Q represents a $C_1$-$C_4$ alkoxy.

7. The composition of claim 6 in which the 6-amino-2-(substituted phenyl)-5-substituted-4-pyrimidinecarboxylate herbicide is 6-amino-2-(4-chloro-2-fluoro-3-methoxyphenyl)-5-methoxypyrimidine-4-carboxylic acid methyl ester.

8. The composition of claim 1 in which the safener is fenchlorazole-ethyl.

9. The composition of claim 1 in which the safener is mefenpyr-diethyl.

10. A method of protecting a wheat or barley from the harmful effects of a 6-amino-2-(substituted phenyl)-5-substituted-4-pyrimidinecarboxylate herbicide of the formula (I)

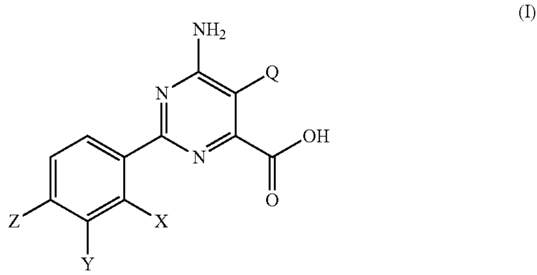

wherein:

Q represents a $C_2$-$C_4$ alkenyl or $C_1$-$C_4$ alkoxy;

X represents H or halogen;

Y represents H, halogen, $C_1$-$C_4$ alkoxy, or —$NR_1R_2$;

Z represents halogen, C1-C4 alkyl or C1-C4 haloalkyl; and $R_1$ and $R_2$ independently represent H or $C_1$-$C_4$ alkyl;

or an agriculturally acceptable salt, ester, or amide derivative thereof, which comprises contacting the wheat or barley with, or applying to the area under cultivation, in addition to the 6-amino-2-(substituted phenyl)-5-substituted-4-pyrimidinecarboxylate herbicide, a safener selected from fenchlorazole, fenchlorazole-ethyl, mefenpyr, mefenpyr-diethyl, and mixtures thereof, wherein the weight ratio of the safener to the 6-amino-2-(substituted phenyl)-5-substituted-4-pyrimidinecarboxylate herbicide is in the range of 1:16 to 4:1.

11. The method of claim 10 in which the weight ratio of the safener to 6-amino-2-(substituted phenyl)-5-substituted-4-pyrimidinecarboxylate herbicide is in the range of 1:4 to 2:1.

12. The method of claim 10 in which the 6-amino-2-(substituted phenyl)-5-substituted-4-pyrimidinecarboxylate herbicide is selected from the group consisting of 6-amino-2-(4-chloro-2-fluoro-3-methoxyphenyl)-5-vinyl pyrimidine-4-carboxylic acid; 6-amino-2-(4-trifluoromethyl phenyl)-5-methoxypyrimidine-4-carboxylic acid; 6-amino-2-(4-chloro-2-fluoro-3-methoxyphenyl)-5-methoxypyrimidine-4-carboxylic acid; 6-amino-2-p-tolyl-5-methoxypyrimidine-4-carboxylic acid; 6-amino-2-(4-chloro-3-dimethylamino-2-fluorophenyl)-5-vinylpyrimidine-4-carboxylic acid: 6-amino-2-(4-chloro-3-fluorophenyl)-5-methoxypyrimidine-4-carboxylic acid; 6-amino-2-(4-chloro-2,3-difluorophenyl)-5-methoxypyrimidine-4-carboxylic acid; and agriculturally acceptable salts, esters, or amides thereof.

13. The method of claim 10, wherein Q represents a $C_2$-$C_4$ alkenyl.

14. The method of claim 13 in which the 6-amino-2-(substituted phenyl)-5-substituted-4-pyrimidinecarboxylate herbicide is 6-amino-2-(4-chloro-2-fluoro-3-methoxyphenyl)-5-vinylpyrimidine-4-carboxylic acid methyl ester.

15. The method of claim 10, wherein Q represents a $C_1$-$C_4$ alkoxy.

16. The method of claim 15, in which the 6-amino-2-(substituted phenyl)-5-substituted-4-pyrimidinecarboxylate herbicide is 6-amino-2-(4-chloro-2-fluoro-3-methoxyphenyl)-5-methoxypyrimidine-4-carboxylic acid methyl ester.

17. The method of claim 10 in which the safener is mefenpyr-diethyl.

18. The method of claim 10 in which the safener is fenchlorazole-ethyl.

* * * * *